Figure 7:
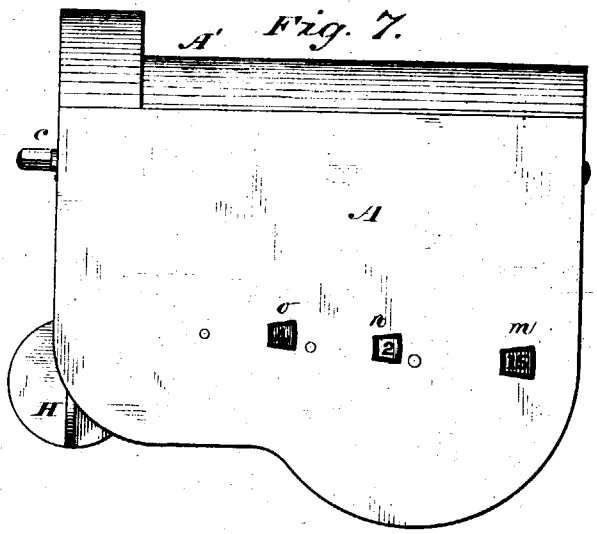

2 Sheets—Sheet 1.
W. H. HORNUM,
Assignor, by mesne assignments, to THE RAILWAY REGISTER MANUFACTURING CO.
Fare Register.
No. 9,371. Reissued Sept. 7, 1880.
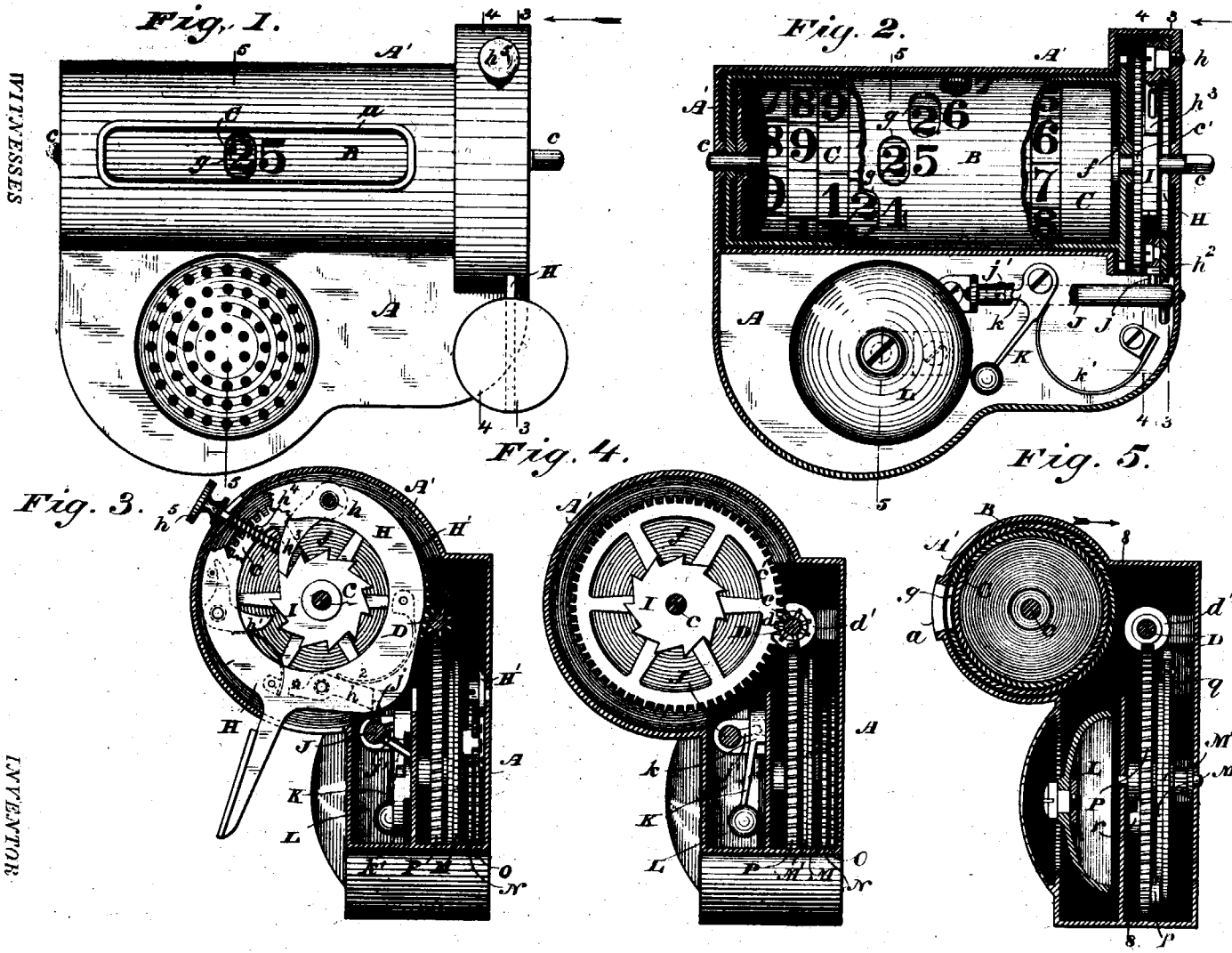
WITNESSES
Wm. A. Skinkle
L. B. Wright.
INVENTOR
William H Hornum,
By his Attorneys
Baldwin, Hopkins & Peyton.

W. H. HORNUM,

Assignor, by mesne assignments, to THE RAILWAY REGISTER MANUFACTURING CO.

Fare Register.

No. 9,371. Reissued Sept. 7, 1880.

WITNESSES

Wm. A. Smith,
L. B. Wright.

INVENTOR

William H. Hornum,

By his Attorneys

Baldwin, Hopkins & Peyton.

UNITED STATES PATENT OFFICE.

WILLIAM H. HORNUM, OF NEW YORK, ASSIGNOR, BY MESNE ASSIGNMENTS, TO THE RAILWAY REGISTER MANUFACTURING COMPANY, OF BUFFALO, N. Y.

FARE-REGISTER.

SPECIFICATION forming part of Reissued Letters Patent No. 9,371, dated September 7, 1880.

Original No. 171,133, dated December 14, 1875; Reissue No. 8,014, dated December 25, 1877. Application for reissue filed June 22, 1880.

*To all whom it may concern:*

Be it known that I, WILLIAM H. HORNUM, a citizen of the United States, residing in the city, county, and State of New York, have invented certain new and useful Improvements in Fare-Registers, of which the following is a specification.

My invention relates to registering-machines of the class which are operated by the conductor or by the receiver of the fares upon passenger cars or vehicles once for every fare received, so as to tally or count said fares and be a check or monitor upon the collector's honesty, he being thereby compelled to render a true return of fares received or collections made.

An alarm forming part of the register is sounded at each actuation of said register to notify those in the car that a proper registration has been made. If the operator fails to actuate the register once for each fare received his fraudulent practices are soon exposed either through reports of passengers or by means of a detective, who is employed to watch and discover whether the instruments are properly and honestly used to register each and every fare collected.

Fare-registering machines are divided into several classes, one of which is known as the "duplex" class, comprising registers embodying in their organization two or different sets of registering mechanism simultaneously operated by a common actuator or prime mover in connection with an alarm.

One set of the duplex registering mechanism is for the purpose of registering consecutively the fares received upon each trip or direction of travel only of the car or vehicle, and is now commonly known as a "trip-register," it having the capacity of being reset to zero or its starting-point, indicative of no registry, at will, without affecting or disturbing the integrity of the record or tally made by the other set of registering mechanism, so as to commence tallying or registering anew for each trip. The other or second set of said duplex registering mechanism, which is what is now commonly known as a "permanent," "general," or "continuously-counting" register, is for the purpose of registering or tallying consecutively and simultaneously with the trip-register not only the fares collected on one trip, but the fares collected or received on a large number or series of trips of the car or vehicle, said register being incapable of the resetting movements given to the trip-register. It is to this class of duplex machines that my present invention more particularly belongs; and my object is to provide a machine of large registering capacity both as to its trip and general registers, which will be proof against improper or fraudulent manipulation by the conductor or collector.

My said invention consists in certain new combinations and organizations of mechanisms which are recited at the close of the specification.

The accompanying drawings illustrate my said new combinations of mechanism as embodied and organized in the best way known to me at the date of filing my application for the original patent.

Figure 9:
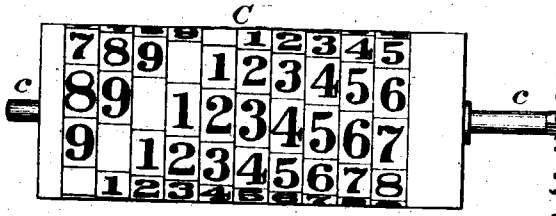
Figure 6:
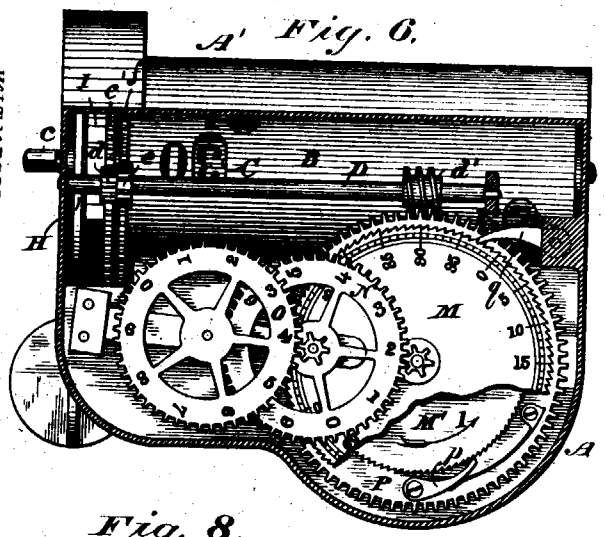
Figure 8:
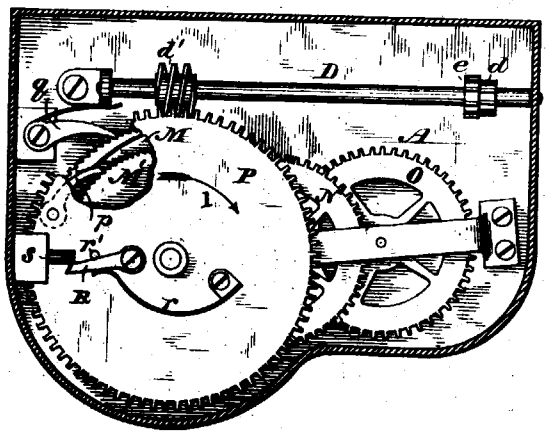

In said drawings, Figure 1 is a front or face view of the apparatus. Fig. 2 is a similar view, partly in section, to show the internal parts more clearly, the front plate or cover also of the alarm apparatus being removed to exhibit a full view of said apparatus. Figs. 3, 4, and 5 are transverse sections through the machine on the lines 3 3, 4 4, and 5 5, respectively, of Figs. 1 and 2, looking in the direction indicated by the arrows on said last-mentioned figures. Fig. 6 is a view from the rear of the machine, the back plate being broken away or removed to show the general or permanent registering mechanism, the face of which is directed toward the back of the casing through windows or openings in which its indications are read; and Fig. 7 is a back view of the machine, showing the said windows or openings, which permit inspection of the count or tally of the general register, as alluded to in the description of Fig. 6. Fig. 8 is a sectional view taken on the line 8 8 of Fig. 5, looking in the direction indicated by the arrow, the view showing more especially the yielding "zero-stop," so termed by me, which constitutes one of the important elements of my improved machine; and Fig. 9 is a view of the inner cylinder, forming part of the trip-register mechanism detached.

The casing which incloses the operative parts of my improved register consists in the organization I have shown of a rectangular or straight-sided portion, A, which contains the alarm mechanism and the general-register mechanism, and of a cylindrical portion, A′, which contains the trip-register mechanism.

This trip-register preferably consists of two cylinders or portions, B C, organized to work one inside the other in the interior of the cylindrical portion A′ of the register-casing, the said casing being provided in front with a rectilinear slot, *a*, extending nearly its whole length, as shown in Fig. 1, so as to plainly expose the record made by the trip-register.

The inner cylinder or under portion, C, is firmly mounted or fixed upon an axle, arbor, or shaft, *c*, which has its bearing in the heads or ends of the casing A′. The outer cylinder or top portion, B, which surrounds the cylinder C, revolves loosely upon the said axle *c*.

A spur or cog-wheel, *c′*, is firmly secured or fixed upon the axle *c* of the cylinder C, near one end, which wheel gears or meshes with a pinion-wheel, *d*, fixed upon a shaft, D, mounted in bearings near the upper end of the casing A, and running parallel with the axle *c* of the trip-register. A second pinion, *e*, is fixed upon said shaft D, and gears or meshes with a cog-wheel, *f*, secured to the end of the cylinder B, the proportions between the cog-wheels *c′ f* and pinions *d e* being such that when the inner cylinder, C, is turned the outer cylinder, B, will be caused to move in the same direction, but at a different speed from that of the said inner cylinder.

The surface or periphery of the inner cylinder, C, is divided off into one hundred spaces, arranged in ten rows, which extend in slightly-oblique directions from one end of the cylinder to the other, or nearly so. Each row contains ten spaces and the figures from 1 to 9, one space in each row being left blank. (See Fig. 9.)

The outer cylinder, B, is marked with the figures from 0 to 9, which are arranged on a spiral line extending all around said cylinder on the sides of openings *g*, Figs. 1 and 2, which are also arranged on a spiral line running parallel to the line of the figures, so as to permit one number of the inner cylinder at a time to be read through said openings.

It will be understood from this description that the two cylinders constituting the trip-register can be turned to such a position that one of the blank spaces of the inner cylinder comes under the opening alongside the 0 or zero indication on the outer cylinder and in line with the slot *a* in the casing. If the inner cylinder is then turned so as to bring successively its blank spaces in line with the slot *a*, while the outer cylinder is turned by its gearing to bring successively the figures 1, 2, 3, &c., in line with said slot, the trip-register will indicate the figures 0 to 9. As the motion continues the spaces of the inner cylinder, containing the figures 1, are successively brought in line with the slot *a*, and at the same time the figures 0 to 9 on the outer cylinder come in line with said slot, as before, in registering units, and the apparatus registers, counts, or tallies the numbers 10 to 19, and so on, as the actuation of the machine is proceeded with in registering consecutively, one after another, the fares as they are received or collected, the trip-register being capable of registering 99 fares.

It will be understood that the motion of the two cylinders may be easily regulated by the gearing (cog-wheels *c′ f* and pinions *d e*) so as to produce the desired result, according to the manner in which the figures are placed on the inner and outer cylinders, which may be changed in various ways.

In the example illustrated in the drawings, motion is given to the trip-register by a finger-lever, H, constituting the actuator or prime mover of the machine, said lever being pivoted at *h*, and carries an actuating-pawl, *h′*, that engages, when the lever is depressed, with a ratchet-wheel, I, secured to the cog-wheel *c′* of the cylinder C.

The movement of the lever H sufficiently far to move the trip-register one point or indication also simultaneously operates the alarm apparatus by a pawl, $h^2$, which engages a crank-arm, *j*, of a rock-shaft, J, so as to rock said shaft and bring a cam or projection, *j′*, thereof in contact with a projection, *k*, of the pivoted hammer-arm K, to raise and trip said hammer-arm and to permit it to strike the bell L of the alarm apparatus. A spring, *k′*, as usual, throws the bell-hammer when tripped against the bell with force sufficient to sound the alarm to notify those in the car that the register has been actuated and the fare tallied. As soon as the pressure of the finger upon the lever is removed it is automatically returned to its normal position, in readiness for a new actuation of the register and alarm by means of a suitable spring, H′, as is common in registering apparatus.

In order to prevent back movement of the trip-register during its counting operation a pawl, $h^3$, is pivoted upon the same axis as the lever H, and is held in contact with the actuating ratchet-wheel I by a suitable spring, $h^4$, as is usual in registering apparatus.

As the trip-register is operated consecutively in the process of counting, the general register, through the medium of the shaft D (which carries a worm-wheel, *d′*) and a pawl-and-ratchet arrangement, is also operated consecutively, the tally of the general register being similar to that of the trip-register. In other words, if the trip-register has been actuated so as to indicate the collection of, say, twenty fares, the general register will also indicate the same number, or a like increase over the record previously made and preserved by it at the moment of commencing a new tally on the trip-register; and this feature of simultaneous and consecutive operation of the trip and general registers is a characteristic essential in perfect duplex fare-registers, inasmuch as it is necessary that one register should constitute a check upon the other, in order to prevent fraudulent operations on the part of the collector in manipulating the machine.

The said general register is shown as consisting of a train of three wheels, M, N, and O, geared together and provided with numerals on their faces, which are read through openings or windows *m n o*, respectively, in the back plate of the casing of the register, as shown in Fig. 7. The first of said wheels, M, is capable of registering ninety-nine fares before it reaches the zero-point; the next wheel, N, registers hundreds—that is to say, it is moved one point or indication (of which there are ten) at every complete revolution of the wheel M; and the next wheel, which is the wheel O, registers thousands—that is to say, it is moved one point or indication (of which there are ten) at every complete revolution of the wheel N in the process of counting, whereby the general register is capable of registering consecutively nine thousand nine hundred and ninety-nine fares, which is a capacity I have deemed to be amply sufficient.

The first wheel, M, of the general register is actuated, as aforesaid, through the medium of the shaft D, the worm-wheel *d'* of which meshes with and turns a cog-wheel, P, turning loosely around or about the same axis as the wheel M, the wheel P being provided with a pivoted pawl, *p*, upon its side next the registering-wheel M, which engages with the teeth of a ratchet-wheel, M', firmly connected with or forming part of said registering-wheel M. When said cog-wheel P is turned in the direction indicated by the arrows 1 in Figs. 6 and 8, which is in a direction corresponding with the counting direction of the trip-register, the pawl *p* will compel the counting-wheel M to travel forward in its counting direction also and register the same number as the trip-register does and at the same time, while if said cog-wheel P is turned in the opposite direction, which corresponds with the direction of the trip-register when being turned backward to reset it, the pawl *p* will move or slip over the teeth of the ratchet-wheel M' without affecting it, the general register-train being locked from back movement by a pawl or detent, *q*, which engages the ratchet-teeth formed on the periphery of the counting-wheel M, as shown in Figs. 6 and 8.

The trip-register is reset to zero or to the point indicative of no registration independently of the prime-mover alarm and general register by means of the shaft *c*, which constitutes the axis of the trip-register, said shaft being squared at one end for the reception of a key, which may be turned to carry the trip-register backward to zero at the end of each trip, the locking pawl or detent $h^3$ being removed from contact with the teeth of the ratchet-wheel I by means of a finger-piece, $h^5$, (shown in Fig. 3,) which is a well-known instrumentality in registering-machines.

I have found that it is necessary in duplex fare-registers, in order to prevent fraudulent manipulation of the register, that the trip-register be prevented from being reset or moved round by the resetting mechanism farther than the zero-point, while it should have the capacity of moving forward when actuated by the prime mover of the apparatus in connection with the general register in its counting operation past the zero-point, if desired, without obstruction.

If the conductor could, at the beginning of the trip, with the trip-register at zero, turn the trip-register past the zero-point by the resetting mechanism until it indicated any desired number—for example, eight—and at the time of entering the car he should find twenty passengers, he could collect the whole number of fares and only register twelve of them upon the machine, using a false alarm for the remaining eight, if necessary. The figures of the trip-register which are exposed would then agree with the number of passengers in the car and apparently be an honest record, while the general register would show a record of but twelve fares, or that increase over its former record. Should twenty more fares be taken during the remainder of the trip they could all be registered, and the trip-register would show a record of forty fares, while the general register would show only thirty-two, or a like increase over its former record. To make both registers agree the conductor would only have to turn the trip-register to show thirty-two, while he could pocket the amount of eight fares.

To prevent any such manipulation of a duplex register I have provided mechanism which prevents resetting of the trip-register beyond zero by the resetting mechanism, while permitting said register to be moved past zero with the general register in the process of counting or tallying only, and, as far as I know, I am the first ever to have accomplished this result.

The zero-stop mechanism I have shown consists of a plate or piece, R, pivoted to the cog-wheel P on the side opposite to that which carries the general-register actuating-pawl *p*, said plate being acted upon by a spring, *r*, to hold it up against a fixed pin or lug, *r'*, projecting from said wheel P. The face of said plate R is inclined, so that when the wheel P is turned forward in the direction indicated by the arrow marked thereon, which is in the direction to register upon the trip and general registers, said plate will yield and slip past a fixed stop or pin, *s*, projecting from the register-casing, and will offer no obstruction to the forward motion of the wheel, and consequently will not interfere with the working of the registering mechanism; but if the trip-register is reset or turned back, as at the end of a trip, to bring it to zero or the starting-point, the cog-wheel P will turn in the opposite direction to that indicated by the arrows, Figs. 6 and 8, independently of the general register until the plate R strikes the fixed stop *s*, which offers an absolute bar to its farther movement, the organization of the zero-stop being such that the single-trip register is arrested at zero.

The yielding zero-stop is applicable to duplex registering mechanism of various construction, and its advantage over a rigid zero-stop is that it allows of turning the registering mechanism forward to any desired extent in the counting process, while the rigid zero-stop arrests the registering mechanism when said mechanism is moved forward in the counting process as well as when it is turned backward in the resetting operation. If the capacity of the trip-register is only 100, no more than this number can be registered with the rigid zero-stop; but with the yielding zero-stop there is no limit to the trip-register, since every time said register is moved forward one step the general register is also moved, and consequently, if the trip-register is turned beyond 100, so that it shows 18 or any other number, the general register will at once expose the correct number.

I do not claim in this reissue of my original patent a rigid zero-stop in combination with the duplex registering mechanism of a fare-register, such being shown and claimed in the Reissue No. 8,013 of my original Patent No. 165,832, of July 20, 1875.

I claim herein as of my invention—

1. The combination, substantially as hereinbefore set forth, of a trip-register, a general register, an actuator for actuating said registers simultaneously for consecutive counting, and mechanism which permits said trip-register to be moved past the zero-point in the counting operation without obstruction while preventing movement of said register past the zero-point when reset or moved independently of the general register.

2. The combination, substantially as hereinbefore set forth, of a trip-register, a general register, an alarm, an actuator for actuating said registers simultaneously for consecutive counting, and for sounding the alarm for each actuation of the registering mechanism, and mechanism which permits said trip-register to be moved past the zero-point in the counting operation without obstruction, while preventing movement of said register past the zero-point when reset or moved independently of the general register.

3. The combination, substantially as hereinbefore set forth, of a trip-register capable of being set to zero, an alarm mechanism, an actuator for actuating said register for consecutive counting and for simultaneously sounding the alarm for each actuation of the register, and mechanism which permits said register to be moved past the zero or starting point in the counting process while preventing its movement past said point when reset independently of said alarm apparatus and actuator.

4. The combination, substantially as hereinbefore set forth, of a trip-register, an actuator for actuating said register for consecutive counting, a device independent of the counting-actuator to reset said trip-register, and mechanism which permits said register to be moved past its zero or starting point in the process of counting while preventing its movement past said point when reset.

5. The combination, substantially as hereinbefore set forth, of a trip-register, a general register, an alarm, an actuator for actuating said registers simultaneously for consecutive counting and for operating the alarm for each actuation of the registers, a device for resetting said trip-register independently of the general register, alarm, and actuator, and mechanism which permits the trip-register to be moved beyond its zero or starting point in the counting process, but prevents movement of said register beyond said point during its resetting operation.

6. The combination, substantially as hereinbefore set forth, of a trip-register, a general register, a ratchet-and-pawl connection which permits the two registers to be moved simultaneously by a common actuator or prime mover in the process of consecutive counting while enabling the trip-register to be returned or reset to zero independently of the general register, and mechanism which permits said trip-register to be moved past the zero-point with the general register in the counting process, but prevents its movement past that point when being reset.

7. The combination, substantially as hereinbefore set forth, of a register-casing having an opening or window, a register for consecutive counting consisting of different numbered portions, one of which covers the other, is provided with a series of figures arranged on a spiral line, and is capable of permitting inspection through it of the figures on the covered portion, and mechanism to move said counting portions to exhibit the consecutive indications of the register through the opening or window in the casing.

8. The combination, substantially as hereinbefore set forth, with a general register capable of consecutive counting, of a trip-register, also capable of consecutive counting, consisting of different numbered counting portions, one of which covers the other, is provided with a series of figures arranged on a spiral line, and is adapted to permit inspection through it of the figures on the covered portion of the register.

9. The trip-register constructed, substantially as hereinbefore set forth, of two numbered counting portions geared together so as to move at different speeds in an inclosing-casing having an opening or window, one of said counting portions being divided off into a series of numbered spaces and covered by the other counting portion, while the said covering portion is provided with numbers arranged in a spiral line opposite similarly-arranged openings, which openings permit inspection of the figures on the covered counting portion of the register.

10. The combination, substantially as hereinbefore set forth, of the trip-register, the general register, an actuating ratchet-wheel, by which said trip-register is simultaneously moved with the general register in the process of consecutive counting, the actuator having a pawl to act upon said ratchet-wheel, and mechanism which permits the trip-register to be moved past the zero or starting point in the counting process without obstruction while stopping said trip-register at said point when reset or moved independently of the counting-actuator.

11. The combination, substantially as hereinbefore set forth, of the trip-register, the general register, the actuating ratchet-wheel by which said trip-register is moved simultaneously with the general register in the process of consecutive counting, the actuator carrying a pawl to act upon said ratchet-wheel, the alarm actuated once for each actuation of said trip-register, and mechanism which permits the trip-register to be moved past the zero or starting point in the counting process without obstruction while stopping said trip-register at said point when reset or moved independently of the counting-actuator.

In testimony whereof I have hereunto subscribed my name.

WILLIAM H. HORNUM.

Witnesses:
EUGENE E. OUDIN,
THOS. T. SHERMAN.